(12) United States Patent
Tan

(10) Patent No.: US 7,906,148 B2
(45) Date of Patent: Mar. 15, 2011

(54) LATEX MEDICAL ARTICLES FOR RELEASE OF ANTIMICROBIAL AGENTS

(75) Inventor: Sharon Mi Lyn Tan, Brighton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1811 days.

(21) Appl. No.: 10/631,871

(22) Filed: Jul. 31, 2003

(65) Prior Publication Data

US 2005/0025800 A1    Feb. 3, 2005

(51) Int. Cl.
*A61K 9/50* (2006.01)
(52) U.S. Cl. ............................................ 424/501
(58) Field of Classification Search .................. None
See application file for complete search history.

(56) References Cited

U.S. PATENT DOCUMENTS

| | | | |
|---|---|---|---|
| 4,592,920 A | 6/1986 | Murtfeldt | 427/2 |
| 4,902,503 A | 2/1990 | Umemura et al. | 424/83 |
| 5,180,585 A | 1/1993 | Jacobson et al. | 424/405 |
| 5,451,424 A * | 9/1995 | Solomon et al. | 427/2.1 |
| 6,191,192 B1 | 2/2001 | Monden et al. | 523/122 |
| 6,329,444 B1 | 12/2001 | McGlothlin et al. | 523/105 |
| 6,342,212 B1 | 1/2002 | Schuette et al. | 424/78.1 |
| 6,368,611 B1 | 4/2002 | Whitbourne et al. | 424/411 |
| 6,585,767 B1 | 7/2003 | Holley et al. | 623/2.41 |
| 2002/0016585 A1 | 2/2002 | Sachse | 604/544 |
| 2002/0142093 A1 | 10/2002 | Gibson et al. | 427/213.3 |
| 2002/0155158 A1 | 10/2002 | Lewis et al. | 424/486 |
| 2002/0155310 A1 | 10/2002 | Li et al. | 428/494 |
| 2002/0160109 A1 | 10/2002 | Yeo et al. | 427/213.3 |
| 2002/0187175 A1 | 12/2002 | Petrea et al. | 424/404 |
| 2003/0017211 A1 | 1/2003 | Steiner et al. | 424/499 |
| 2003/0017286 A1 | 1/2003 | Williams et al. | 428/35.2 |
| 2003/0031728 A1 | 2/2003 | Martin et al. | 424/618 |
| 2003/0118664 A1 | 6/2003 | Trogolo et al. | 424/618 |

FOREIGN PATENT DOCUMENTS

JP            09111053          4/1997

OTHER PUBLICATIONS

Matsumura, Yoshinobu et al., "Mode of Bactericidal Action of Silver Zeolite and Its Comparison with That of Silver Nitrate," Applied and Environmental Microbiology, vol. 69, No. 7, Jul. 2003, pp. 4278-4281.

* cited by examiner

*Primary Examiner* — Carlos A Azpuru
(74) *Attorney, Agent, or Firm* — Mayer & Williams PC; David B. Bonham; Keum J. Park

(57) ABSTRACT

According to an aspect of the present invention, a medical article is provided which comprises a latex antimicrobial region. The latex antimicrobial region can constitute the entirety of the medical article, or it can constitute only a portion of the medical article. The latex antimicrobial region comprises release-modulating microparticles, which are dispersed within a latex polymer. The release-modulating microparticles further comprise an antimicrobial agent, and the microparticles are adapted to release the antimicrobial agent. Examples of medical articles that can be produced in accordance with the present invention are gloves, finger cots, supply and drainage tubes, catheters, condoms, and contraceptive diaphragms. Also described are methods for forming such articles.

23 Claims, No Drawings

LATEX MEDICAL ARTICLES FOR RELEASE OF ANTIMICROBIAL AGENTS

FIELD OF THE INVENTION

This invention relates to antimicrobial latex compositions. More particularly, the present invention relates to antimicrobial latex compositions suitable for use in connection with medical articles and having sustained antimicrobial activity.

BACKGROUND OF THE INVENTION

Numerous latex medical articles are known, which are required to sustain their aseptic properties over a prolonged period of time. One solution to this problem is to produce a medical article containing a dispersed antimicrobial agent, which releases the antimicrobial agent over an extended period.

It is known that certain heavy metals such as gold, silver, copper and zinc as well as compounds thereof exert an antimicrobial effect upon a wide spectrum of microorganisms, including various bacteria and fungi, at very low metal ion concentrations. This effect is called an oligodynamic effect. Moreover, medical devices have been produced which take advantage of this effect. See, e.g., U.S. Pat. No. 4,902,503, the disclosure of which is incorporated by reference.

Nonetheless, there is continuing need for antimicrobial latex medical articles containing antimicrobial agents, which are released from the articles in a sustained fashion so as to maintain the antimicrobial properties of the same.

SUMMARY OF THE INVENTION

The above and other needs in the art are addressed by the medical articles of the present invention.

According to an aspect of the present invention, a medical article is provided which comprises a latex antimicrobial region. The latex antimicrobial region comprises release-modulating microparticles, which are dispersed within a latex polymer. The release-modulating microparticles further comprise an antimicrobial agent and are adapted to release the antimicrobial agent.

Some examples of medical articles that can be produced in accordance with the present invention are gloves, finger cots, supply and drainage tubes, catheters, condoms, and contraceptive diaphragms.

In certain embodiments, the microparticles comprise an encapsulating layer, for example, a polymer-containing layer, surrounding a region that comprises an antimicrobial agent, for example, an antimicrobial-agent-containing core.

In certain other embodiments, the microparticles comprise a material within which the antimicrobial compound is dispersed. The material can be, for example, a polymeric material or an inorganic material.

Antimicrobial agents providing silver ions, for example, silver-containing zeolite particles, are used in certain embodiments.

The latex polymer can be formed from various latexes (or "latices"), which can be, for example, natural or synthetic.

Other aspects of the invention concern processes for forming the antimicrobial regions of the present invention. For example, an antimicrobial region can be formed by a process that comprises: (a) providing a latex that contains the above release-modulating microparticles, (b) contacting this latex with a substrate, and (c) curing the latex, thereby forming the antimicrobial region. The substrate can be, for example, a mold, which is dipped into the latex.

The present invention is advantageous in that medical articles can be provided, which reduce the potential for infection upon contact with the body of a subject.

Another advantage of the present invention is that latex medical articles can be provided in which the therapeutic agent is dispersed throughout the medical article.

Yet another advantage of the present invention is that latex medical articles can be provided, which release antimicrobial agent over a prolonged period of time.

These and other embodiments and advantages of the present invention will become immediately apparent to those of ordinary skill in the art upon review of the Detailed Description and claims to follow.

DETAILED DESCRIPTION OF THE INVENTION

According to an aspect of the present invention, a medical article is provided which comprises a latex antimicrobial region. The latex antimicrobial region can constitute the entirety of the medical article, or it can constitute only a portion of the medical article. The latex antimicrobial region comprises release-modulating microparticles, which are dispersed within a latex polymer. The release-modulating microparticles further comprise an antimicrobial agent, and they are adapted to modulate the release of the antimicrobial agent.

A wide range of microparticle loadings can be used in connection with the medical articles of the present invention, with the amount of loading being readily determined by those of ordinary skill in the art. Microparticle loadings can range, for example, from 0.1 to 40 wt/o.

By "microparticle" is meant a small particle, typically ranging from 0.01 to 1000 microns in largest dimension, more typically 0.1 to 100 microns. The microparticles can be of any shape, including spherical, elongated, irregular, etc.

The medical articles for use in conjunction with the present invention are typically medical articles that are adapted for contact with a patient, for example, a vertebrate animal, preferably a human. Medical articles for use in conjunction with the present invention include surgical gloves, examination gloves, finger cots, supply and drainage tubes, catheter balloons, uterine thermal ablation balloons, catheter cuffs, condoms, contraceptive diaphragms, in-dwelling urinary drainage catheters, male external urinary drainage catheters, and so forth.

As used herein a "latex polymer" is a polymer, which is formed from a latex. "Latex," as the term is used herein, is an aqueous polymer dispersion. By "aqueous polymer dispersion" is meant a dispersion of polymer particles in a water-containing fluid.

Various methods are known for producing latexes (or "latices"), which can be used in connection with the present invention. Latexes can be, for example, (a) derived from natural sources, in which case the latex is commonly referred to as a "natural latex," (b) prepared by emulsion polymerization, in which case the resulting product is commonly referred to as a "synthetic latex", or (c) prepared from a previously formed polymer, in which case the resulting product is commonly referred to as a "synthetic pseudolatex."

Latices for use in connection with the present invention can be formed from a variety of polymers. For example, the polymer may be a homopolymer or a copolymer (including alternating, random and block copolymers), cyclic, linear or branched (e.g., polymers have star, comb or dendritic architecture), natural or synthetic. The polymers for use in connection with the present invention are typically biostable polymers. A biostable polymer is one that maintains its structural integrity, at least for the time period during which the medical device is in contact with the body.

Accordingly, polymers for latices useful in connection with the present invention include natural polymers and synthetic polymers, examples of which include homopolymers and copolymers of vinyl monomers and diene monomers, for instance, ethylene, styrene, isobutylene, vinyl acetate, vinyl chloride, vinylidiene chloride, acrylonitrile, methacrylate, vinyl pyridine, methyl vinyl ether, butadiene, carboxylated butadiene, neoprene, isoprene (natural polyisoprene is a common example), chloroprene, 1,3-pentadiene, 1,5-hexadiene, 1,6-heptadiene, as well as blends and copolymers (e.g., acrylonitrile-butadiene or styrene-isobutylene copolymers) thereof.

Antimicrobial agents useful for the practice of the present invention include triclosan, chlorhexidine, nitrofurazone, benzalkonium chlorides, and silver ions. Sources for silver ions include numerous silver-containing antimicrobial agents such as silver protein; silver salts such as silver bromide, silver fluoride, silver lactate and silver nitrate; as well as other sources of silver ions including silver-based ion-exchange materials such as silver-ion containing zeolites available as ZEOMIC® from Sinanen Zeomic Co. Ltd., Nagoya, Japan and AgION™ from AgION Technologies, Inc., silver-based glasses such as IONPURE® silver-substituted glasses available from Ishizuka Glass Co., Tokyo, Japan, NOVARON, silver zirconium phosphate available from Taogosei, Nagoya, Japan and AlphaSan® silver-based zirconium phosphates available from Milliken & Company, Spartanburg, S.C., USA; as well as other silver-based inorganic compounds such as IRGAGUARD™ B5000 from Ciba Specialty Chemicals, Basel, Switzerland, JMAC™, porous sintered rutile titanium dioxide containing silver chloride, available from Johnson Matthey, United Kingdom, and MircoFree® inorganic particles from DuPont, which contain silver on a core of zinc oxide or contain silver/copper oxide/zinc sulfate on a core of titanium dioxide or barium sulfate.

As noted above, the selected antimicrobial agent is provided in association with release-modulating microparticles. For instance, in certain embodiments of the invention, the selected antimicrobial agent is provided in association with release-modulating microparticles, which can comprise, for example, a polymeric shell that encapsulates the antimicrobial agent, a polymeric matrix within which the antimicrobial agent is dispersed, or both. Techniques for providing such microparticles include solvent evaporation or extraction (typically in connection with emulsification, e.g., single or double emulsion techniques), coacervation (including simple and complex coacervation), hot melt encapsulation, interfacial crosslinking, interfacial polymerization, spray drying, and so forth. Such techniques are well known. See, e.g., U.S. Patent Appln. No. 20020160109, which is incorporated by reference.

Numerous polymers can be used in connection such release-modulating microparticles, including the polymers listed above. Additional exemplary polymers, not necessarily exclusive of the above polymers, include the following: polyolefins such as metallocene catalyzed polyethylenes, polypropylenes, and polybutylenes and copolymers thereof; vinyl aromatic polymers such as polystyrene; vinyl aromatic copolymers such as styrene-isobutylene copolymers and butadiene-styrene copolymers; ethylenic copolymers such as ethylene vinyl acetate (EVA), ethylene-methacrylic acid and ethylene-acrylic acid copolymers where some of the acid groups have been neutralized with either zinc or sodium ions (commonly known as ionomers); polyacetals; chloropolymers such as polyvinylchloride (PVC); fluoropolymers such as polytetrafluoroethylene (PTFE); polyesters such as polyethyleneterephthalate (PET); polyester-ethers; polyamides such as nylon 6 and nylon 6,6; polyamide ethers; polyethers; elastomers such as elastomeric polyurethanes and polyurethane copolymers; silicones; polycarbonates; and mixtures or copolymers of any of the foregoing.

As seen from the above, the release-modulating microparticles can comprise a polymer-containing shell or matrix to influence release. In other embodiments, the antimicrobial agent is released from microparticles that comprise inorganic materials. Examples include microparticles formed from inorganic, silver-based, ion-exchange materials such as those discussed above, for instance, silver-ion containing zeolites, silver-based glasses, silver-based zirconium phosphates, and sintered titanium dioxide/silver chloride. In each of these examples, the antimicrobial agent (i.e., silver ions) is released from an inorganic material (e.g., zeolites, glasses, zirconium phosphates, porous titanium dioxide).

Once selected, the latex and the antimicrobial-agent releasing microparticles are typically combined using any of a number of methods including, for example, simple mixing. If desired, the latex can be provided with numerous supplemental agents known in the art, including pH adjustors, curing agents, curing accelerators, vulcanization agents, softening agents, bulking agents, antioxidants, colorants, coacervating agents, cationic, anionic, zwitterionic and nonionic surfactants, and so forth.

The mixture is then applied to a suitable substrate (e.g., a medical device substrate or a mold) using any of a variety of techniques including casting techniques, spin coating techniques, web coating techniques, spraying techniques, dipping techniques, techniques involving coating via mechanical suspension, including air suspension, and combinations of these processes. Subsequently, water is either removed or allowed to evaporate from the resulting product, forming a latex polymer. In many embodiments, the latex polymer is cured by heating. In such embodiments, silver-containing antimicrobial agents are advantageous in than they can withstand high curing temperatures, without an associated loss in efficacy.

A specific embodiment of the present invention will now be described, in which dip-molding of a medical article is performed. In this embodiment, a latex is utilized which comprises a natural rubber latex admixed with silver-containing zeolite particles. Among other constituents, vulcanization agents, for example, sulfur-containing compounds, may be added to promote vulcanization. Where natural rubber latex is utilized, proteins from its natural source typically remain in the rubber. Hence, natural rubber latices are often treated to reduce their protein content. One method of achieving this is by washing with water. For example, a double centrifuge processing method is known in which a first centrifuge step removes some of the aqueous phase from the natural rubber latex, followed by the addition of water and a second centrifuge step to remove the added water and additional protein as well. Other methods are known for reducing protein content that involve the use of enzymes to digest the proteins.

A mold, for example, one formed from ceramic or metal, is dipped in the latex, followed by removal of the water, which is assisted by heating the mold. If desired, the dipping and water removal may be performed in repeated cycles to increase film thickness, if desired. Moreover, the thickness of the final medical article is also increased in some embodiments though the use of a coagulant, which is also applied by dipping, either before or after the latex dipping step, usually before.

The film thus formed is then typically vulcanized to bring the rubber to a cured state. In some embodiments, pre-vulcanization (i.e., vulcanization of the rubber in the latex medium prior to the dipping step) is practiced. A film from a pre-vulcanized latex dipping medium does not require vulcanization after the dipping step, but instead only drying to remove the water. In some procedures, both pre- and post-vulcanization are used. Subsequently, the resulting product is removed from the mold. (In some embodiments, a powder such as cornstarch is applied to the mold to assist with release of the product from the mold.)

This procedure can be used to form any number of medical articles. In one particular embodiment, the procedure is used to create a latex balloon sleeve for a catheter.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical article that comprises an antimicrobial region, said antimicrobial region comprising release-modulating microparticles dispersed within a latex polymer, said release-modulating microparticles comprising an antimicrobial agent and being adapted to release the antimicrobial agent, wherein said microparticles comprise a core and an encapsulating layer surrounding said core or wherein the microparticles comprise a material within which the antimicrobial compound is dispersed.

2. The medical article of claim 1, wherein said medical article is selected from gloves, finger cots, supply and drainage tubes, catheters, condoms and contraceptive diaphragms.

3. The medical article of claim 1, wherein said medical article is a balloon catheter.

4. The medical article of claim 3, wherein said antimicrobial region is a balloon sleeve.

5. The medical article of claim 1, wherein said antimicrobial region is heat cured.

6. A medical article that comprises an antimicrobial region, said antimicrobial region comprising release-modulating microparticles dispersed within a latex polymer, said release-modulating microparticles comprising an antimicrobial agent and being adapted to release the antimicrobial agent, wherein said antimicrobial region is vulcanized and wherein either said microparticles comprise a core and an encapsulating layer surrounding said core or wherein the microparticles comprise a material within which the antimicrobial compound is dispersed.

7. The medical article of claim 1, wherein said microparticles comprise an encapsulating layer that surrounds a core comprising said antimicrobial agent.

8. The medical article of claim 1, wherein said microparticles comprise a core and an encapsulating layer surrounding said core, wherein said core comprises said antimicrobial agent, and wherein said encapsulating layer comprises a polymer.

9. The medical article of claim 1, wherein said microparticles comprise a polymer, and wherein said antimicrobial compound is dispersed within said polymer.

10. The medical article of claim 1, wherein said microparticles comprise an inorganic material, and wherein said antimicrobial compound is dispersed within said inorganic material.

11. The medical article of claim 10, wherein said antimicrobial compound is dispersed within pores of said inorganic material.

12. The medical article of claim 1, wherein said microparticles comprise a silver-containing ion exchange material.

13. The medical article of claim 1, wherein said microparticles are silver-containing zeolite particles.

14. The medical article of claim 1, wherein said antimicrobial agent comprises silver.

15. The medical article of claim 1, wherein said latex polymer is formed from a natural latex.

16. The medical article of claim 1, wherein said latex polymer is formed from a synthetic latex.

17. The medical article of claim 16, wherein said synthetic latex is a pseudolatex.

18. The medical article of claim 1, wherein said release-modulating microparticles have an average largest dimension, on a weight average basis, ranging from 0.1 to 100 microns.

19. A process for providing the antimicrobial region of claim 1, comprising: (a) providing a latex comprising said microparticles, (b) contacting said latex with a substrate, and (c) curing said latex thereby forming said antimicrobial region.

20. The process of claim 19, wherein said substrate is a mold that is dipped into said latex.

21. A medical article that comprises an antimicrobial region, said antimicrobial region comprising release-modulating microparticles dispersed within a latex polymer, said release-modulating microparticles comprising an antimicrobial agent and being adapted to release the antimicrobial agent, and said release-modulating microparticles selected from the group consisting of microparticles that comprise an encapsulating region that surrounds a region comprising an antimicrobial agent and microparticles that comprise a polymer having an antimicrobial agent dispersed within said polymer.

22. A medical article that comprises an antimicrobial region, said antimicrobial region comprising release-modulating microparticles dispersed within a latex polymer, said release-modulating microparticles comprising an antimicrobial agent and being adapted to release the antimicrobial agent, and said release-modulating microparticles selected from the group consisting of microparticles that comprise an encapsulating region that surrounds a region comprising an antimicrobial agent and microparticles that comprise a polymer having an antimicrobial agent dispersed within said polymer, wherein said antimicrobial region is vulcanized.

23. The medical article of claim 1, wherein said latex polymer comprises a styrene-isobutylene copolymer.

* * * * *